United States Patent [19]

Withers

[11] 4,404,978

[45] Sep. 20, 1983

[54] BI-STRING DENTAL FLOSS HOLDER

[76] Inventor: David L. Withers, 3424 Archer Ct. N.W., Salem, Oreg. 97304

[21] Appl. No.: 356,773

[22] Filed: Mar. 10, 1982

[51] Int. Cl.$^3$ .............................................. A61C 16/00
[52] U.S. Cl. ....................................................... 132/91
[58] Field of Search ................................... 132/90–92, 132/93

[56] References Cited

U.S. PATENT DOCUMENTS

| | | | |
|---|---|---|---|
| 1,623,231 | 4/1927 | Bowling et al. | 132/92 R |
| 1,955,428 | 4/1934 | Ladwig | 132/92 R |
| 2,463,660 | 3/1949 | Turenchalk et al. | 132/91 |
| 3,693,638 | 9/1972 | Ciccarelli | 132/91 |
| 4,002,183 | 1/1977 | Restall | 132/91 |

FOREIGN PATENT DOCUMENTS 247880 of 0000 United Kingdom ............ 132/92 R

Primary Examiner—Gregory E. McNeill
Attorney, Agent, or Firm—Kolisch, Hartwell & Dickinson

[57] ABSTRACT

A tool of the type using dental floss having a handle to which are joined two double-pronged members. Each member is structured to anchor two ends of a run of floss with a length of the run extending between the tips of the associated prongs. When lengths of floss are received by the two pairs of prong tips, these lengths are in spaced-apart, generally parallel, confronting relatioship. In the preferred embodiment, the two floss lengths are relatively adjustable to the extent that one floss length can be moved laterally past the other. Spring biasing is used to hold the floss lengths in predetermined positions relative to one another when in a relaxed state. Other desired positions are achievable through application of appropriate forces.

17 Claims, 7 Drawing Figures

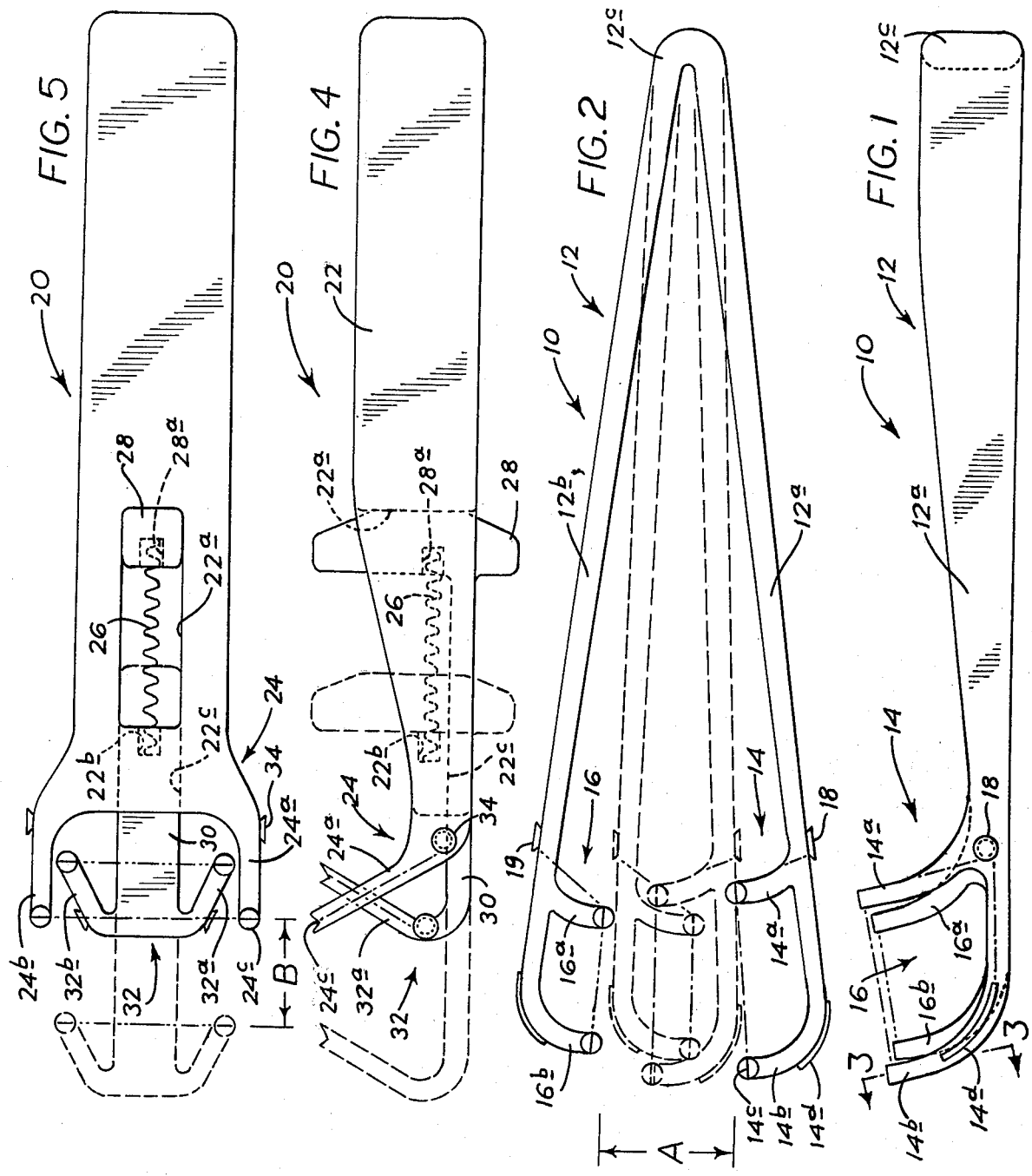

BI-STRING DENTAL FLOSS HOLDER

BACKGROUND AND SUMMARY OF THE INVENTION

This invention pertains to a tool for use in flossing teeth, and in particular, to such a tool having two opposing pairs of prongs adjustable relative to each other to vary the distance between lengths of floss received by each of the pairs of prongs.

The flossing of teeth is now a generally accepted practice for cleaning teeth. The usual procedure includes sliding a tensioned string up and down against a tooth surface which is adjacent an adjoining tooth and therefore difficult to reach with a tooth brush. Flossing is usually performed by manipulating floss only with one's hands. The ends of a run of dental floss of several inches are wrapped around one's index fingers. A length of floss, extending between the fingers under tension, is then inserted into the mouth and forced between adjacent teeth to clean the corresponding tooth surfaces. This is continued until all of the desired tooth surfaces are cleaned. This involves a somewhat awkward and cumbersome process of having to insert one or more fingers inside the mouth to manipulate appropriately the dental floss.

The manual procedure just described has been simplified through the use of devices which provide a pair of spaced-apart prongs, the tips of which have a length of floss extending between them. The prongs are far enough apart to allow the passage of teeth and a portion of the associated jaw without obstruction. These devices therefore provide a means for inserting a length of floss into one's mouth without having to hold the ends of the floss run, and correspondingly, without having to insert one's fingers into the mouth.

Flossing by either of these methods has inherent disadvantages. One is the necessity of applying a single force against the tooth being flossed. This force must be counteracted by the person whose teeth are being flossed. Additionally, it takes several minutes to accomplish the individual flossing of all the appropriate tooth surfaces.

Some people are incapable of flossing adequately his or her own teeth due to lack of training or physical coordination. If so, it is helpful to have another person floss their teeth. If done by hand, one must insert one's own fingers in another's mouth. Additionally, it is difficult to manipulate floss within the small mouth of a young person. The use of the previously mentioned flossing devices partially solves this problem by permitting the introduction of a small clean object in the mouth which is easier to manipulate. It is, however, somewhat difficult to obtain a corresponding degree of cleanliness from flossing compared to a manual system. In addition, the intermittent application of varied forces on a person's jaw can be uncomfortable to that person.

It is therefore a general object of the present invention to overcome the above-described problems in the prior art.

More specifically, it is an object to facilitate the expedient flossing of teeth by providing for the flossing of two tooth sides concurrently.

It is also an object to provide a tooth flosser that can be used with a minimum net force being applied to a person's jaw during the flossing operation. It is thus an object to provide a flosser which flosses both sides of a tooth simultaneously, regardless of its size.

It is further desired to provide such a flosser which accommodates extended circumferential tooth surface contact by the floss.

It is also an object to provide such a tool which is easy to use and inexpensive to manufacture.

One embodiment of this invention has a generally V-shaped handle made of a resilient material. The points of the V each have a pair of spaced-apart prongs which are structured to support, under tension, a length of floss between their extremities. The pairs of prongs are slightly angled toward each other, with the prongs in one pair being closer together and shorter in height than the prongs in the other pair. These features allow passage of the more closely spaced prongs between the wider spaced prongs.

In a second embodiment, a pair of spaced-apart prongs extend from one end of a handle at an obtuse angle relative to the handle. A second pair of prongs is joined to an arm which is disposed slidably on the handle, with this arm being extendible beyond the first pair of prongs. This second pair of prongs extends at an acute angle relative to the handle. Again, one pair of prongs is shorter and more narrowly spaced than the other to allow passage between the more widely separated prongs.

Both of these embodiments provide for the concurrent use of two lengths of floss for cleaning teeth. Thus, they allow for cleaning of two tooth surfaces at a time. This may involve opposite sides of a single tooth, adjacent surfaces of adjacent teeth, or corresponding surfaces of adjacent teeth. When used to clean opposite surfaces of a single tooth or adjacent surfaces of adjacent teeth, the net horizontal force applied on a person's jaw is essentially zero, since equal and opposite forces are being applied. When the tool is used to clean both sides of a single tooth, the prong tip pairs may be moved past each other to effect a more complete wrapping of the corresponding floss lengths around the tooth surfaces. This produces a more complete cleansing of the tooth.

These and additional objects and advantages of the present invention will be more clearly understood from a consideration of the drawings and the detailed description of the preferred embodiments which follow.

BRIEF DESCRIPTION OF THE DRAWINGS

FIG. 1 is a view from a side elevation of a first preferred embodiment made in accordance with this invention.

FIG. 2 is a view taken from the top side of FIG. 1.

FIG. 3 is a cross-sectional view taken along line 3—3 in FIG. 1.

FIG. 4 is a view from a side elevation of a second preferred embodiment.

FIG. 5 is a view taken from the top side of FIG. 4.

FIGS. 6A and 6B are simplified schematics showing (under different conditions) the relative positions of prong tips, floss lengths and a tooth's outline during a typical flossing operation—FIG. 6A showing the relative positions of these elements prior to flossing, and FIG. 6B showing their relative positions during flossing.

DETAILED DESCRIPTION OF THE INVENTION

Referring initially to FIGS. 1-3, and explaining construction of a first-preferred embodiment of the present invention, shown generally at 10 is a dental flossing tool. Tool 10 includes a generally V-shaped handle 12 having handle portions 12a, 12b which are joined at handle end 12c. Extending generally upwardly from the other handle portion ends and generally inwardly toward each other are a pair of double-pronged fork members 14, 16, joined to portions 12a, 12b, respectively. The two members, also referred to herein as dual floss-holding means, each includes a pair of spaced-apart prongs. Prongs 14a, 14b are associated with member 14. Similarly, prongs 16a, 16b are associated with member 16. As can be seen from the drawings, prongs 16a, 16b are shorter and more closely spaced than are prongs 14a, 14b. For reasons to be discussed later, it is necessary that prongs 16a, 16b be close enough together to permit the passage of their tips or extremeties between the tips of prongs 14a, 14b. Both pairs of prongs must be spaced far enough apart to allow passage therebetween of a person's teeth and a portion of the associated jaw without obstruction.

FIG. 3 shows a cross-sectional view of prong 14b. At the tip of the prong is a notch 14c, a feature which exists on all four prongs. It can be seen in FIG. 1 that prongs 14b and 16b have an intermediate bend or elbow. Along each prong elbow is an arcuate ridge such as ridge 14d on prong 14b, which projects outwardly from the prong in such a way as to form a groove, such as groove 14e formed by ridge 14d and prong 14b as shown in the figures. Along the outer sides of the bases of members 14, 16 are discs 18, 19, respectively, which have a reverse conical frustum shape. The angle between the surface of the member and the adjoining edge of the disc is of a small enough angle to form a nip region for string the size of dental floss.

In the preferred construction of this first embodiment of the invention, the tool is made unitarily of a fairly rigid, though resilient material such as a hard plastic or metal. The handle portions are constructed to provide for a separation between the prong pairs as represented by the distance "A" in FIG. 2, of approximately ½ inch when in a relaxed state position. This is found to be wide enough to accommodate receipt of a large person's widest tooth therebetween.

Referring now to FIGS. 4 and 5 and explaining the construction of a second preferred embodiment of the present invention, shown generally at 20 is a dental flossing tool having a unitary elongate handle 22. Rigidly fixed to the left-hand end of the handle, as viewed in the figures, is a first fork member 24 having a first pair of spaced-apart prongs 24a, 24b. The tips of the two prongs have notches which extend in a common line, such as notch 24c on prong 24a. Prongs 24a, 24b extend at an angle which is obtuse with respect to the general longitudinal axis of handle 22.

Handle 22 has a cavity 22a which opens to opposite sides of handle 22 as shown. Additionally, a bore 22b extends partially into handle 22 through the side of cavity 22a nearest to member 24, as shown in FIGS. 4 and 5. Bore 22b is sized to receive one end of a helical spring 26 which is also referred to herein as spring-biasing means.

Freely extending through cavity 22a is an elongate knob 28 which projects outwardly from opposite sides of handle 22 as shown. A second bore 28a extends inwardly from the surface of knob 28 closest to member 24 corresponding in position and size with bore 22b for receipt of the other end of spring 26. Spring 26, in its fully extended state (also referred to as a relaxed state), presses knob 28, as shown by solid lines in FIGS. 4, 5, against the edge of cavity of 22a furthest from member 24.

Below bore 22b is a channel 22c which extends from cavity 22a in a direction parallel with the longitudinal axis of handle 22 outwardly through the left end of handle 22 below member 24 as shown.

An elongate arm 30 is joined to knob 28 and extends therefrom slidably through channel 22c and out the left end of handle 22, as shown in the figures. Channel 22c and arm 30 cooperate to form what is also referred to herein as a joining means. Knob 28 in conjunction with channel 22c and arm 30 are also referred to as adjusting means.

Extending upwardly at an acute angle from the left end of arm 30 is a second fork member 32 which includes a second pair of prongs 32a, 32b. These prongs have grooves in their tips similar to groove 24c, previously described. This second pair of prongs is shorter and spaced more closely together than the first pair of prongs. Relative prong construction is similar to that discussed for the first embodiment. Members 24, 32 are also referred to herein as floss-holding means.

As can be seen from viewing the figures, when spring 26 is in its fully extended condition, prongs 32a, 32b are received between the first pair of prongs in such a manner that the tips of prongs 32a, 32b are closer to handle 22 than are those of prongs 24a, 24b. Disposed at the outer base of each prong is a disc, such as disc 34 disposed at the base of prong 24a. These discs have a construction similar to that of disc 18 discussed previously with respect to the first preferred embodiment.

Explaining the operation of the first preferred embodiment and referring to FIGS. 1-3, one end of a run of commercially available dental floss is initially wrapped several times around the base of disc 18. The floss is then placed in groove 14e, up to the outer edge of the tip of prong 14b, through notch 14c, over to the associated notch in the tip of prong 14a and back down to disc 18 where the run is anchored with several more wraps around the base of the disc. The resulting location of the floss is shown by the dash-dot lines in FIGS. 1 and 2. Disc 18 and the portion of handle 12 adjacent its base cooperate to form an anchor or anchoring means for a run of floss. The same procedure is followed to position a run of floss on fork member 16 using disc 19, which floss is shown by the dash-double-dot line in the figures.

With the floss lengths in place, tool 10 is picked up in one's hand for use. By squeezing handle portions 12a, 12b (also referred to as adjusting means) together, the lengths of floss extending between the tips of the two pairs of prongs are caused to come closer together. If sufficient force is placed on the handle portions, the tips of the prongs associated with member 16 pass between the tips of the prongs associated with member 14. This result is illustrated by the dashed lines in FIG. 2. Thus, the two lengths of floss are caused to pass each other. End 12c of handle 12 acts generally as a pivot point for moving the two handle portions and is referred to herein also as hinge means. The resiliency of the two handle portions provides a spring biasing and is therefore also referred to as spring-biasing means. The use of tool 10 for cleaning teeth will be described later.

A similar procedure is performed with respect to tool 20 for installing a run of floss on each pair of prongs. However, as has been discussed with reference to FIGS. 4 and 5, instead of having a single disc on which both ends of a run of floss are anchored, a disc is associated with each prong. Therefore, each disc is used to anchor an end of a run of floss with a length of the floss extending through the associated notches in the tips of the prongs.

When the particular embodiment shown is in a relaxed condition, the prongs 32a, 32b extend through and between prongs 24a, 24b. Tool 20 is picked up with the thumb positioned against the right edge of knob 28, as viewed in FIGS. 4 and 5. By applying a force directed to the left or toward the fork members to overcome the force of spring 26, the floss length associated with member 32 is moved under and past the floss length associated with member 24, until it is in a fully extended position as shown in dashed lines in the figures. For the same reasons discussed with respect to distance A in FIG. 2, the distance B between the floss lengths when member 32 is in this extended position should be approximately equal to ½ inch.

It can be seen that both embodiments provide for moving the two floss lengths relative to each other. The range of movement allows positioning the lengths far enough apart to permit locating them on both sides of a tooth. The lengths may also be moved closer together, even to the extent of moving them past one another.

During the following discussion of the actual use of the dental flossing tools for their intended purpose, it should be clear from the previous discussion that the relative positions of the prong tips, and floss lengths which are operatively received thereon, are essentially the same for both embodiments. Thus, in the following discussions, where reference is made to FIGS. 6A and 6B, prongs 40, 42, 46, 48 will be understood to be equivalent to either prongs 14a, 14b, 16a, 16b, respectively, in the first preferred embodiment or prongs 24a, 24b, 32a, 32b, respectively, in the second preferred embodiment.

Referring first to FIG. 6A, outlined in dashed lines is a tooth 36 as viewed from the top. A longer floss length 38 is shown as a dash-dot line extending between prongs 40, 42. A shorter floss length 44 is shown as a dash-double-dot line extending between prongs 46, 48. A length of floss is stretched between each prong pair on a dental flossing tool as described previously and the floss lengths separated sufficiently to position a floss length on each side of tooth 36. This separation is shown as distance C in FIG. 6A. Floss lengths 38, 44 are then inserted along each side of tooth 36. The prong pairs are moved toward each other causing the floss lengths to wrap around the corresponding surfaces of tooth 36. Dental floss is not normally resilient. However, due to the resiliency of the material which the tool is made of, the prongs flex inwardly, allowing for the wrapping of the floss around the tooth. The wrapping can be improved by installing the floss between the prongs only tight enough to hold it in position. This allows for increased flexing of the prongs during the flossing operation and therefore permits the prongs to be drawn closer together, if not past each other. This increases the amount of tooth surface contact area covered by the floss during flossing. FIG. 6B shows this wrapped-around position in which the prong pairs have been moved past each other in order to provide for improved tooth coverage.

It can be seen from viewing FIG. 6B that the force applied by the two lengths of floss are directed inwardly toward each other through tooth 36. There is thus no net horizontal (in the plane of the figures) force on the jaw to which the tooth is connected.

Once the floss lengths are in the positions shown in FIG. 6B, the floss lengths are slid along the tooth surfaces alternately in reverse directions normal to the plane of the figure. This loosens the build-up of foreign material on the tooth. This procedure is preferably repeated for each tooth in a person's mouth.

It is anticipated that numerous other constructions of a dental flossing tool made in conformance with this invention are possible. One variation could include a tool having scissor-type handles. Additionally, the prong pairs could be attached hingedly to a fixed handle with means provided for pivoting the prong extremeties toward and away from each other. Thus, while the invention has been particularly shown and described with reference to the foregoing preferred embodiments, it will be understood by those skilled in the art that other changes in form and detail may be made therein without departing from the spirit and scope of the invention as defined in the following claims.

It is claimed and desired to secure by Letters Patent:

1. A tool of the type using dental floss or the like for use in flossing teeth comprising
   a handle,
   and dual floss-holding means joined to said handle for supporting, under tension, a pair of lengths of floss in spaced-apart, generally parallel, confronting relationship, said dual floss-holding means being structured for simultaneously and unobstructedly disposing such supported lengths of floss adjacent common-jaw tooth surfaces.

2. The tool of claim 1 which further includes means for adjusting the distance between lengths of floss operatively supported by said floss-holding means.

3. The tool of claim 2, wherein said floss-holding means and adjusting means are constructed to enable the moving of one floss length past the other floss length when such lengths are operatively supported by said holding means.

4. A tool of the type using dental floss or the like for use in flossing teeth comprising
   an elongate handle,
   a pair of double-pronged fork members joined to said handle, each member having a pair of spaced-apart prongs constructed to receive a length of a run of floss extended between extremeties of the prongs in the pair, with lengths of floss so received by said two members residing in spaced-apart, generally parallel, confronting relationship, said fork members being structured for simultaneously and unobstructedly disposing such supported lengths of floss adjacent common-jaw tooth surfaces, and
   for each fork member, means for anchoring opposite ends of a floss run associated with a length of floss extended between the extremeties of the associated prongs, thus to facilitate tensioning of such a length.

5. The tool of claim 4 which further includes means for adjusting the distance between lengths of floss operatively received by said two members.

6. The tool of claim 5, wherein said members and adjusting means are constructed to enable the moving of one floss length past the other floss length when such lengths are operatively received by said members.

7. The tool of claim 5, wherein said adjusting means includes hinge means.

8. The tool of claim 5, wherein said adjusting means includes means joining slidably at least one of said members to said handle.

9. The tool of claim 5 which further includes spring-biasing means for holding said prongs in said pairs in predetermined positions relative to one another when in a relaxed state and, when said pairs are displaced from said predetermined position, for applying a force directed toward returning the prongs to the relaxed-state condition.

10. A dental flossing tool for use with dental floss or the like comprising
    a generally V-shaped handle having a pair of joined, elongate handle portions,
    a pair of spaced-apart prongs joined to and extending from each portion, said pairs of prongs being constructed to receive a length of a run of floss extended between extremeties of the prongs in the pair, with lengths of floss so received by said two pairs of prongs residing in spaced-apart, generally parallel, confronting relationship, said pairs of prongs being structured for simultaneously and unobstructedly disposing such supported lengths of floss adjacent common-jaw tooth surfaces, and
    for each pair of prongs, means for anchoring opposite ends of a run of floss associated with a length of floss operatively extended between the extremeties of the associated prongs, thus to facilitate tensioning of such a length.

11. The tool of claim 10, wherein said handle portions are moveable with respect to each other such that the spacing between lengths of floss operatively received by said extremeties is thereby adjustable.

12. The tool of claim 11, wherein said prong pairs and handle portions are constructed to enable the moving of one floss length past the other floss length when such lengths are operatively received by said extremeties.

13. The tool of claim 11, wherein said handle portions are spring biased to hold said prong pairs a predetermined distance apart when in a relaxed state and, when displaced from said predetermined position, to apply a force directed toward returning said prongs to said relaxed-state condition.

14. A dental flossing tool for use with dental floss or the like comprising
    an elongate handle,
    a first pair of prongs extending from one end of said handle having spaced-apart extremeties which are constructed to receive, under tension, a length of floss,
    an elongate arm having a first end joined to said one end of said handle,
    a second pair of prongs joined to and extending from a second end of said arm, said second pair of prongs also having spaced-apart extremeties which are constructed to receive, under tension, a length of floss,
    said arm and second pair of prongs being constructed so that a length of floss operatively received thereon is in spaced-apart, generally parallel, confronting relationship with respect to a length of floss operatively received by said first pair of prongs for simultaneously and unobstructedly disposing such supported lengths of floss adjacent common-jaw tooth surfaces, and
    for each pair of prongs, means for anchoring opposite ends of a run of floss associated with a length of floss operatively extended between the extremeties of the associated prongs, thus to facilitate tensioning of such a length.

15. The tool of claim 14, wherein said arm is joined slidably to said handle to provide for adjustment of the distance between lengths of floss operatively supported by each pair of prongs.

16. The tool of claim 15, wherein said second pair of prongs and said arm are constructed to enable the moving of a length of floss operatively received by said second pair of prongs past a length of floss operatively received by said first pair of prongs.

17. The tool of claim 15 which further includes spring-biasing means for holding lengths of floss operatively supported by said pairs of prongs a predetermined distance apart when in a relaxed state, and when displaced therefrom, to apply a force directed toward returning said pairs of prongs to said relaxed-state condition.

* * * * *